United States Patent
Bulatowicz

(10) Patent No.: US 10,416,245 B2
(45) Date of Patent: *Sep. 17, 2019

(54) OPTICAL PUMP BEAM CONTROL IN A SENSOR SYSTEM

(71) Applicant: Michael D. Bulatowicz, Sun Prairie, WI (US)

(72) Inventor: Michael D. Bulatowicz, Sun Prairie, WI (US)

(73) Assignee: NORTHROP GRUMMAN SYSTEMS CORPORATION, Falls Church, VA (US)

( * ) Notice: Subject to any disclaimer, the term of this patent is extended or adjusted under 35 U.S.C. 154(b) by 432 days.

This patent is subject to a terminal disclaimer.

(21) Appl. No.: 15/080,876

(22) Filed: Mar. 25, 2016

(65) Prior Publication Data

US 2017/0276741 A1    Sep. 28, 2017

(51) Int. Cl.
| | |
|---|---|
| G01R 33/26 | (2006.01) |
| G01R 33/032 | (2006.01) |
| G01C 19/62 | (2006.01) |
| G01R 33/00 | (2006.01) |
| G01N 24/00 | (2006.01) |

(52) U.S. Cl.
CPC ............ *G01R 33/26* (2013.01); *G01C 19/62* (2013.01); *G01R 33/0041* (2013.01); *G01R 33/0322* (2013.01); *G01N 24/006* (2013.01)

(58) Field of Classification Search
CPC ............ G01C 19/62; G01R 33/26; G04F 5/14
See application file for complete search history.

(56) References Cited

U.S. PATENT DOCUMENTS

| | | | |
|---|---|---|---|
| 4,157,495 A | 6/1979 | Grover et al. | |
| 4,525,672 A | 6/1985 | Lam et al. | |
| (Continued) | | | |

FOREIGN PATENT DOCUMENTS

| | | | |
|---|---|---|---|
| EP | 2749895 A1 | 7/2014 | |
| EP | 2749895 A1 * | 7/2017 | ............ G01R 33/26 |

OTHER PUBLICATIONS

European Search Report for corresponding EP 17 16 1708 completed Aug. 8, 2017.

(Continued)

*Primary Examiner* — Alesa Allgood
(74) *Attorney, Agent, or Firm* — Tarolli, Sundheim, Covell & Tummino LLP

(57) ABSTRACT

One example includes a sensor system. A cell system includes a pump laser which generates a pump beam to polarize alkali metal vapor enclosed within a sensor cell. A detection system includes a probe laser to generate a probe beam. The detection system can calculate at least one measurable parameter based on characteristics of the probe beam passing through the sensor cell resulting from precession of the polarized alkali metal vapor in response to an applied magnetic field. A pump beam control system pulsewidth modulates a frequency of the pump beam to provide a pulse-width modulated (PWM) pump beam, and controls a duty-cycle of the PWM pump beam based on the characteristics of the probe beam passing through the sensor cell in a feedback manner to control polarization uniformity of the alkali metal vapor and to mitigate the effects of AC Stark shift on the at least one measurable parameter.

14 Claims, 3 Drawing Sheets

(56) References Cited

U.S. PATENT DOCUMENTS

| | | | |
|---|---|---|---|
| 4,544,891 A | 10/1985 | Karwacki | |
| 5,537,671 A | 7/1996 | Toyama et al. | |
| 8,742,964 B2 | 6/2014 | Kleks et al. | |
| 9,077,354 B2* | 7/2015 | Strabley | G04F 5/14 |
| 9,229,073 B2* | 1/2016 | Walker | G01R 33/26 |
| 9,970,999 B2* | 5/2018 | Larsen | G01R 33/26 |
| 2005/0206377 A1* | 9/2005 | Romalis | G01R 33/02 324/301 |
| 2007/0247241 A1* | 10/2007 | Braun | G04F 5/14 331/94.1 |
| 2008/0106261 A1* | 5/2008 | Romalis | G01R 33/24 324/304 |
| 2009/0066430 A1* | 3/2009 | Braun | G04F 5/14 331/94.1 |
| 2010/0156547 A1 | 6/2010 | McGuyer et al. | |
| 2013/0328557 A1* | 12/2013 | Larsen | G01R 33/26 324/304 |

OTHER PUBLICATIONS

Affolderbach, et al. "Light Shift Reduction in Atomic Clocks"; Society for Optical Engineering—Laser and Information Technologies, SPIE, PO Box 10 Bellingham WA 98227-0010 USA, vol. 5449, 2004, pp. 342-349, XP040186167, * the whole document *.
Fang, et al.: "Light-Shift Measurement and Suppression in Atomic Spin Gyroscope"; Applied Optics, Optical Society of America, Washington, DC; US, vol. 51, No. 31, Nov. 1, 2012 (Nov. 1, 2012), pp. 7714-7717, XP001579352, ISSN: 0003-6935, DOI: 10.1364/AO.51.007714 [retrieved on Nov. 1, 2012] * the whole document *.
European Office Action for Application No. 16 150 518.5 dated Jun. 19, 2019.

* cited by examiner

OPTICAL PUMP BEAM CONTROL IN A SENSOR SYSTEM

TECHNICAL FIELD

The present invention relates generally to sensor systems, and specifically to optical pump beam control in a sensor system.

BACKGROUND

Sensor systems, such as nuclear magnetic resonance (NMR) gyroscopes and magnetometers and/or electron paramagnetic resonance (EPR) magnetometers, can include a cell that contains one or more alkali metal vapors, such as rubidium or cesium, together with one or more nuclear spin isotopes that are caused to precess in response to a magnetic field. The alkali metal vapor(s) can be stimulated to an excited state in response to optical pumping in a given frequency band. Optical pumping can be off-resonance with respect to an atomic transition wavelength of the alkali metal vapor(s), such as to provide polarization uniformity within the sensor cell. However, off-resonance pumping can also subject the alkali metal vapor to AC Stark shift, in which the atoms of the alkali metal vapor experience a virtual magnetic field that is not experienced by the nuclear spin isotopes. The resultant effect of the AC Stark shift is an added bias in the detected magnetic field of the associated magnetometer or an added bias in the rotation angle and/or rate of the associated gyroscope, and thus errors in their respective measurable parameters. Because alkali metals have two independent ground states, and thus two separate atomic transition frequencies, AC Stark shift is unavoidable in the optical pumping of the alkali metals.

SUMMARY

One example includes a sensor system. A cell system includes a pump laser which generates a pump beam to polarize alkali metal vapor enclosed within a sensor cell. A detection system includes a probe laser to generate a probe beam. The detection system can calculate at least one measurable parameter based on characteristics of the probe beam passing through the sensor cell resulting from precession of the polarized alkali metal vapor in response to an applied magnetic field. A pump beam control system pulse-width modulates a frequency of the pump beam to provide a pulse-width modulated (PWM) pump beam, and controls a duty-cycle of the PWM pump beam based on the characteristics of the probe beam passing through the sensor cell in a feedback manner to control polarization uniformity of the alkali metal vapor and to mitigate the effects of AC Stark shift on the at least one measurable parameter.

Another embodiment of the invention includes a method for substantially mitigating AC Stark shift effects in a sensor system configured to calculate at least one measurable parameter. The method includes generating a circularly-polarized pump beam and pulse-width modulating a frequency of the pump beam about a center frequency to provide a PWM pump beam having a duty-cycle. The method also includes providing the PWM pump beam through a sensor cell to polarize an alkali metal vapor enclosed within the sensor cell to facilitate precession of the alkali metal vapor via a magnetic field and providing a linearly-polarized probe beam through the sensor cell. The method also includes demodulating a Faraday rotation of a detection beam corresponding to the linearly-polarized probe beam exiting the sensor cell based on the duty-cycle to determine a time-averaged frequency of the PWM pump beam over a pulse-width modulation period of the PWM pump beam. The method further includes controlling the duty-cycle of the PWM pump beam based on the demodulated Faraday rotation to adjust the time-averaged frequency to substantially stabilize and mitigate the effects of AC Stark shift on the at least one measurable parameter.

Another embodiment of the invention includes a sensor system. The system includes a cell system comprising a pump laser configured to generate a pump beam to polarize alkali metal vapor enclosed within a sensor cell and to facilitate precession of the alkali metal vapor in response to an applied magnetic field. The pump beam can be provided through the sensor cell at an offset angle relative to the applied magnetic field. The system also includes a detection system comprising a probe laser configured to generate a probe beam. The detection system can be configured to calculate at least one measurable parameter based on characteristics of the probe beam passing through the sensor cell resulting from precession of the polarized alkali metal vapor in response to the applied magnetic field. The system further includes a pump beam control system configured to pulse-width modulate a frequency of the pump beam about a center frequency corresponding to an approximate maximum absorption of the pump beam via the alkali metal vapor to provide a PWM pump beam having a duty-cycle, to demodulate a detection beam corresponding to the probe beam exiting the sensor cell based on the duty-cycle, and to control the duty-cycle of the PWM pump beam based on the demodulated detection beam in a feedback manner to control polarization uniformity of the alkali metal vapor and to mitigate the effects of AC Stark shift on the at least one measurable parameter.

DETAILED DESCRIPTION

Figure 1:
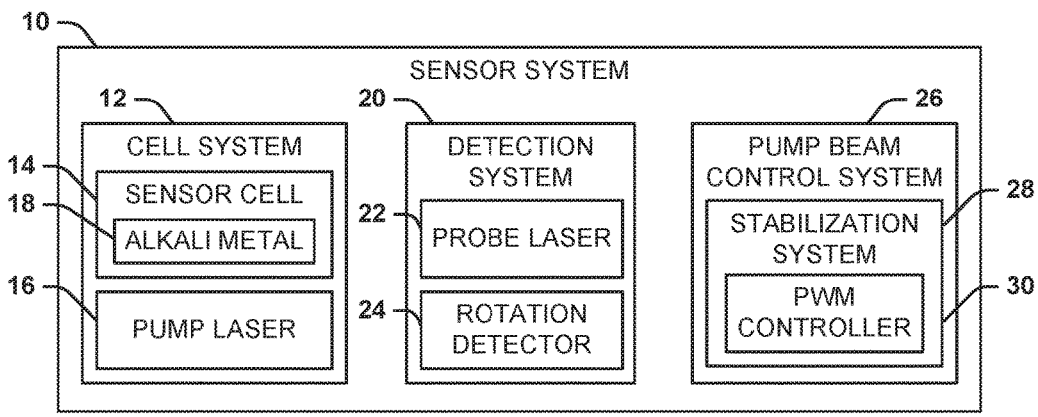
FIG. 1 illustrates an example of a sensor system.

The present invention relates generally to sensor systems, and specifically to optical pump beam control in a sensor system. A sensor system, such as a nuclear magnetic resonance (NMR) gyroscope, an NMR magnetometer, or an electron paramagnetic resonance (EPR) magnetometer, can include a cell system that includes a pump laser configured to generate a pump beam to polarize alkali metal particles enclosed within a sensor cell. A detection system can be configured to calculate at least one measurable parameter, such as rotation about a sensitive axis or an external magnetic field, based on precession of the polarized alkali metal particles in response to an applied magnetic field. As an example, the precession of the polarized alkali metal particles can be coupled with precession of nuclear spin isotopes such as xenon (e.g., $^{129}$Xe or $^{131}$Xe), such that the Larmor precession frequency and/or phase information of the one or more nuclear spin isotopes can be extracted to calculate the measurable parameter. The sensor system can also include a pump beam control system configured to monitor optical absorption of the pump beam passing through the sensor cell and to pulse-width modulate a frequency of the pump beam to substantially mitigate the effects of AC Stark shift on the at least one measurable parameter based on the pulse-width modulated (PWM) pump beam.

The monitoring of the optical absorption can be based on linearly polarized light associated with the pump beam exiting the sensor cell being incident on a photodetector, such as can be associated with circularly polarized optical pump light passing through an appropriately oriented quarter-wave plate. A center frequency of the PWM pump beam can be set to approximately a frequency value of substantial maximum absorption of the pump beam passing through the sensor cell, such that the pulse-width modulation of the pump beam can be between first and second frequencies that are substantially equal and opposite the center frequency through a given pulse-width modulation period of the duty-cycle. The PWM pump beam can induce a virtual magnetic field within the sensor cell that affects the precession of the alkali metal particles in a manner that is associated with the AC Stark shift effects at the first and second frequencies associated with the duty-cycle. Therefore, a probe beam that is provided through the sensor cell that can exhibit characteristics associated with the at least one measurable parameter can exhibit a Faraday rotation at each of the first and second frequencies. Therefore, the Faraday rotation can be demodulated based on the duty-cycle to generate a DC error signal corresponding to the effects of the AC Stark shift. Accordingly, the duty-cycle of the PWM pump beam can be adjusted (e.g., digitally) based on the DC error signal to maintain the duty-cycle such that the effects of the AC Stark shift are equal and opposite with respect to the time duration of the first and second frequencies of the PWM pump beam in a feedback manner. As a result, the AC Stark shift is substantially stabilized, such that the time-averaged effects of the AC Stark shift are substantially mitigated with respect to the at least one measurable parameter.

FIG. 1 illustrates an example of a sensor system 10. As an example, the sensor system 10 can correspond to one or more of a nuclear magnetic resonance (NMR) gyroscope, an NMR magnetometer, an electron paramagnetic resonance (EPR) magnetometer, or a combination thereof. The sensor system 10 can be implemented in any of a variety of applications, such as detection, guidance, and/or aviation systems. As another example, the sensor system 10 can be implemented as a portion of an overall sensor application, such as can be configured to operate in multiple axes.

The sensor system 10 includes a cell system 12 that includes a sensor cell 14 and a pump laser 16. The sensor cell 14 can be, for example, a glass casing of any of a variety of shapes and sizes. The sensor cell 14 includes an alkali metal 18, as well as one or more nuclear spin isotopes (not shown) in the case of an NMR sensor. As an example, the alkali metal 18 can be rubidium (Rb) vapor, such as $^{85}$Rb, or cesium (Cs) vapor, such as $^{133}$Cs, and the nuclear spin isotope(s) can include noble gas isotopes such as helium (He), krypton (Kr), and/or xenon (Xe) (e.g., $^{3}$He, $^{83}$Kr, $^{129}$Xe, and/or $^{131}$Xe). The pump laser 16 can be configured to generate an optical pump beam that is circularly-polarized and directed through the sensor cell 14 via a set of optics to stimulate (i.e., excite) the particles of the alkali metal 18 to a spin-polarized state. The spin-polarized particles of the alkali metal 18 can precess in the sensor cell 14 in response to an applied magnetic field (e.g., an AC and/or DC magnetic field applied along a sensitive axis), such as may be generated by the precessing nuclear spin isotopes. For example, the polarized particles of the alkali metal 18 can experience EPR precession due to a DC or AC magnetic field along an EPR sensitive axis (e.g., the X- and/or Y-axis) that is stimulated by the applied magnetic field (e.g., a DC and AC magnetic field resonant with the EPR Larmor precession frequency along the EPR insensitive Z-axis), and the nuclear spin isotopes can precess about the applied magnetic field (e.g., a DC magnetic field along the EPR insensitive Z-axis) in response to a magnetic field resonant with the NMR Larmor precession frequency or frequencies applied in the X-Y plane. Furthermore, the sensor cell 14 can also include one or more buffer gases.

The sensor system 10 also includes a detection system 20 that is configured to calculate at least one measurable parameter. For example, the measurable parameter can include rotation about a sensitive axis in the example of the sensor system 10 being configured as an NMR gyroscope, or can include a vector magnitude of an external magnetic field in the example of the sensor system 10 being configured as an NMR and/or EPR magnetometer. In the example of FIG. 1, the detection system 20 includes a probe laser 22 and a rotation detector 24. The probe laser 22 can be configured to generate a probe beam that passes through the sensor cell 14. The precession of the particles of the alkali metal 18 and the associated nuclear spin isotopes can result in polarization phase changes associated with the probe beam exiting the sensor cell 14 (e.g., based on interaction between the photons from the probe laser 22 and the particles of the alkali metal 18). Therefore, the detection system 20 can calculate the measurable parameter based on changes in the precession of the particles of the alkali metal 18, such as resulting from rotation of the sensor cell 14 or an external magnetic field, such as based on the rotation detector 24 determining a Faraday rotation of the probe beam.

The particles of the alkali metal 18 can be subject to AC Stark shift, in which the optical pumping of the particles of the alkali metal 18 via the pump laser 16 is off-resonance with respect to atomic transition wavelengths corresponding to two independent ground states of the alkali metal 18. The AC Stark shift can cause a virtual magnetic field that is experienced by the alkali metal 18 but not by the nuclear spin isotopes, which causes a change to the precession of the particles of the alkali metal 18 relative to the nuclear spin isotopes. As a result, the AC Stark shift exhibits an added bias to the measurable parameter that is calculated by the detection system 20. The virtual magnetic field is added to the applied magnetic field, such that if the AC Stark shift is stable, and if the sensor system 10 is tuned to an optimum operating point, the sensor system 10 experiences substantially no scale factor or bias errors arising from AC Stark shift effects. However, changes in intensity, frequency, and/or alignment of the optical pump beam, as well as vapor density of the alkali metal 18 (e.g., based on temperature of the sensor cell 14), can result in changes in the virtual magnetic field caused by the AC Stark shift, and thus changes in an overall magnitude of the applied magnetic field experienced by the alkali metal 18.

In the example of the sensor system 10 being configured as a magnetometer, the sensitive axes of the magnetometer are defined based on an interaction of the particles of the alkali metal 18 relative to the applied magnetic field, as determined by the detection system 20. For example, the detection system 20 can demodulate a detection signal at a typically fixed phase relationship with the applied magnetic field, such that changes in the phase of the precession of the particles of the alkali metal 18 result in changes to the detection signal based on interaction of the probe beam and the precessing particles of the alkali metal 18 in the sensor cell 14. However, the effect of an unstable AC Stark shift with respect to changing the precession of the particles of the alkali metal 18 can result in a change in the magnetometer signal phase that can be perceived as components of an external magnetic field in vector angles rotated about the sensitive axis.

In the example of the sensor system 10 being configured as a gyroscope, magnetic field feedback can be implemented to substantially null any detected magnetic fields in a cross-axis relative to the sensitive axis to maintain alignment of the sensitive axis to the applied magnetic field. Thus, a virtual magnetic field in a cross-axis direction caused by unstable AC Stark shift can be indistinguishable from a real magnetic field, such that the feedback system can generate a real magnetic field to offset the perceived virtual magnetic field. As described previously, the nuclear spin isotopes in the sensor cell 14 are not subject to effects of the virtual magnetic field, but are subject to the effects of a real magnetic field generated to offset the virtual magnetic field. As a result, the offset real magnetic field can cause misalignment, and thus instability, of the sensitive axis of the gyroscope. Furthermore, the presence of AC Stark Shift effects can alter the phase of the precession of the particles of the alkali metal 18 with respect to the precession of the nuclear spin isotopes. This phase offset can result in a phase offset in the feedback for stimulation of the precession of the nuclear spin isotopes, which can result in an angular rate bias.

To substantially stabilize and mitigate the effects of AC Stark shift, the sensor system 10 includes a pump beam control system 26. The pump beam control system 26 includes a stabilization system 28 that includes a pulse-width modulation (PWM) controller 30. The stabilization system 28 is configured to pulse-width modulate the frequency of the optical pump beam provided by the pump laser 16 via the PWM controller 30 to provide a PWM pump beam, such that the absorption of the PWM pump beam passing through the sensor cell 14 varies inter alia as a function of the instantaneous frequency of the pump beam during a duty-cycle of the PWM pump beam. The pump beam controller 26 is also configured to monitor the absorption of the PWM pump beam passing through the sensor cell 14, such as based on a set of optics and a photodetector, to control a temperature of the pump laser 16 to substantially maintain a center frequency of the PWM pump beam at an approximate maximum absorption of the PWM pump beam via the alkali metal vapor 18, thus corresponding to the transition frequencies associated with the independent ground states of the alkali metal 18.

As an example, the stabilization system 28 can initially set a center frequency of the PWM pump beam to be approximately equal to the frequency of substantial maximum absorption. The PWM pump beam can induce a virtual magnetic field internal to the sensor cell 14 that affects the precession of the particles of the alkali metal 18 in a manner that is associated with the AC Stark shift effects, modulated at the duty-cycle of the PWM pump beam. For example, the pump laser 16 can be oriented in a manner to provide components of the induced magnetic field in a plane that is orthogonal to an axis about which the particles of the alkali metal 18 precess, such as based on an offset angle of the PWM pump beam relative to an applied magnetic field based on which the alkali metal vapor 18 precesses. Therefore, the probe beam that is generated by the probe laser 22 can exhibit a Faraday rotation modulated at the duty-cycle in response to the induced virtual magnetic field in addition to a Faraday rotation based on the measurable parameter (e.g., which can occur at a much lower frequency). Therefore, the stabilization system 28 can demodulate the Faraday rotation of the probe beam based on the duty-cycle to generate a DC error signal that can correspond to the effects of the AC Stark shift. Accordingly, the duty-cycle of the PWM pump beam can be shifted based on the DC error signal in a feedback manner to maintain the DC error signal at a zero amplitude corresponding to a value at which the effects of the AC Stark shift are equal and opposite with respect to the duty-cycle, and thus with respect to the two independent ground states of the alkali metal 18, in a feedback manner. Accordingly, based on the feedback adjustment of the duty-cycle of the PWM pump beam by the stabilization system 28, the stabilization system 28 stabilizes the AC Stark shift while optically pumping the alkali metal vapor 18 off-resonance to substantially maximize polarization uniformity in the sensor cell 14. Furthermore, because the AC Stark shift effects are substantially equal and opposite with respect to the product of AC Stark shift magnitude, direction (e.g., positive or negative direction), and duty-cycle in each of the two off-resonance states about the center frequency based on excitation of the alkali metal 18 from the respective two independent ground states of the alkali metal 18, the AC Stark shift effects are substantially mitigated. Accordingly, scale factor and bias errors associated with the measurable parameter(s) of the sensor system 10 is likewise substantially mitigated.

Figure 2:
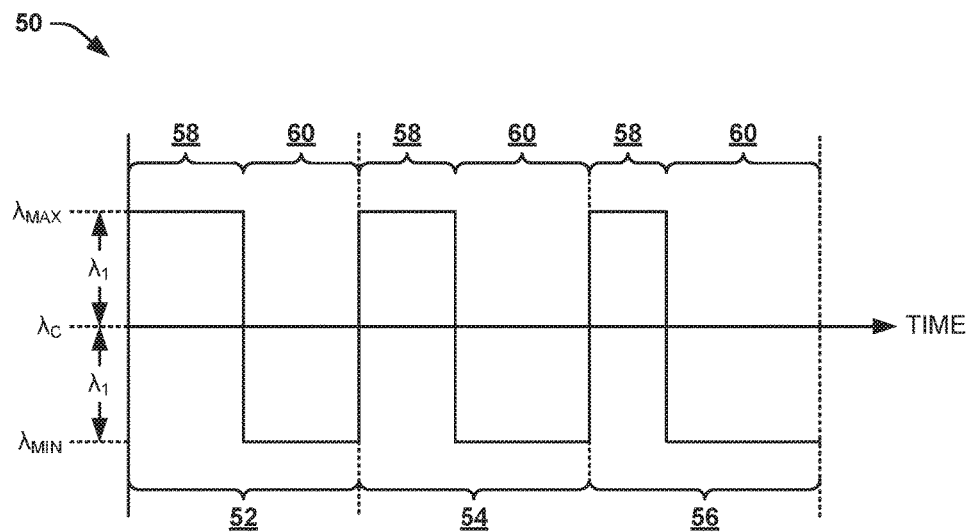
FIG. 2 illustrates an example timing diagram of a pulse-width modulation signal waveform.

FIG. 2 illustrates an example timing diagram 50 of a pulse-width modulation signal waveform. As an example, the diagram 50 demonstrates the modulation signal DTH plotted as a function of time. The modulation signal DTH is demonstrated in the example of FIG. 2 as a square-wave signal oscillating about a center wavelength $\lambda_C$. The modulation signal DTH is demonstrated as having a maximum amplitude corresponding to a first wavelength $\lambda_{MAX}$ and a minimum amplitude corresponding to a second wavelength $\lambda_{MIN}$. In the example of FIG. 2, the first and second wavelengths $\lambda_{MAX}$ and $\lambda_{MIN}$ are separated equally and oppositely about the center wavelength $\lambda_C$ by a wavelength difference $\lambda_1$.

The pulse-width modulation signal waveform demonstrated in the timing diagram 50 can correspond to the PWM pump beam generated by the pump laser 16. Thus, the center wavelength $\lambda_C$ can be a wavelength that corresponds to an approximate maximum absorption of photons of the PWM pump beam by the alkali metal vapor 18, such that each of the wavelengths $\lambda_{MAX}$ and $\lambda_{MIN}$ are off-resonance with respect to a transition wavelength associated with the alkali metal vapor 18. The timing diagram 50 includes a first pulse-width modulation period 52, a second pulse-width modulation period 54, and a third pulse-width modulation period 56 of the PWM pump beam. Each of the pulse-width modulation periods 52, 54, and 56 includes an "ON" time 58 at which the wavelength of the PWM pump beam is at the first wavelength $\lambda_{MAX}$ and an "OFF" time 60 at which the wavelength of the PWM pump beam is at the second wavelength $\lambda_{MIN}$. The pulse-width modulation periods 52, 54, and 56, as well as subsequent pulse-width modulation periods, can have a fixed time duration, such as based on a fixed number of clock cycles.

As an example, based on demodulating a detection beam corresponding to the optical probe beam generated by the probe laser 22 exiting the sensor cell 14, the stabilization system 28 can determine that the DC error signal has a non-zero value. Therefore, the alkali metal vapor 18 is exhibiting deleterious effects of AC Stark shift. In response to the DC error signal having a non-zero value, the stabilization system 28 is configured to adjust the duty-cycle of the PWM pump beam, such as based on digitally adjusting the clock cycles corresponding to "ON" time 58 relative to the "OFF" time 60. In the example of FIG. 2, the stabilization system 28 adjusts the duty-cycle of the pulse-width modulation period 54 relative to the pulse-width modulation period 52 by decreasing the "ON" time 58, and thus increasing the "OFF" time 60 in the pulse-width modulation period 54, such as by adjusting the clock cycles for each of the "ON" time 58 and the "OFF" time 60, based on the DC error signal. As an example, the DC error signal can have a polarity that is indicative of the AC Stark shift based on a time-average of the Faraday rotation of the detection beam over a given pulse-width modulation period.

Subsequently, based on demodulating the detection beam based on the duty-cycle and determining a time-averaged Faraday rotation of the detection beam, the stabilization system 28 can again determine that the DC error signal has a non-zero value. Therefore, the adjustment to the duty-cycle of the pulse-width modulation period 54 was insufficient to negate the deleterious effects of AC Stark shift. In response to the DC error signal having the non-zero value, the stabilization system 28 again adjusts the duty-cycle of the PWM pump beam. In the example of FIG. 2, the stabilization system 28 adjusts the duty-cycle of the pulse-width modulation period 56 relative to the pulse-width modulation period 54 by again decreasing the "ON" time 58, and thus increasing the "OFF" time 60 in the pulse-width modulation period 56, such as by adjusting the clock cycles for each of the "ON" time 58 and the "OFF" time 60, based on the DC error signal. Accordingly, the stabilization system 28 can substantially continuously monitor the detection beam and adjust the duty-cycle of the PWM pump beam in a feedback manner to maintain a zero value of the DC error signal, and thus stabilize the effects of AC Stark shift.

Figure 3:
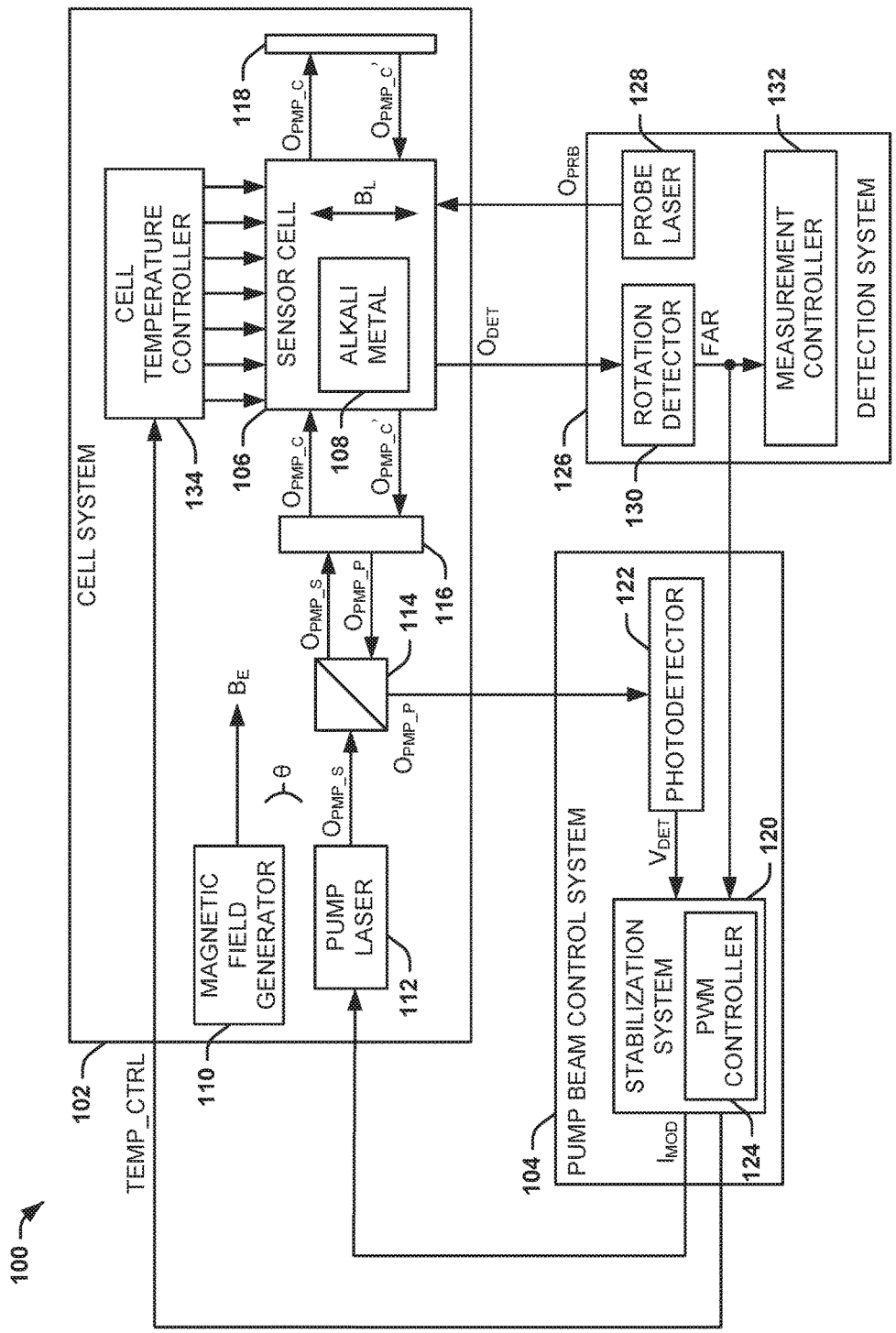
FIG. 3 illustrates another example of a sensor system.

FIG. 3 illustrates another example of a sensor system 100. As an example, the sensor system 100 can correspond to a portion of an NMR gyroscope, an NMR magnetometer, an EPR magnetometer, or a combination thereof. The sensor system 100 can be implemented in any of a variety of applications, such as detection, guidance, and/or aviation systems. As another example, the sensor system 100 can be implemented as a portion of an overall sensor application, such as can be configured to operate in multiple axes.

The sensor system 100 includes a cell system 102 and a pump beam control system 104. In the example of FIG. 3, the cell system 102 includes a sensor cell 106. The sensor cell 106 can be, for example, a glass casing of any of a variety of shapes and sizes. The sensor cell 106 includes an alkali metal 108, as well as one or more nuclear spin isotopes (not shown), in the example of the sensor system 100 being configured as an NMR system. As an example, the alkali metal 108 can be Rb vapor, such as $^{85}$Rb, to substantially reduce a difference between the ground-state transition frequencies of the alkali metal 108 relative to other alkali metal types (e.g., Cs), as described previously in the example of FIG. 2. In addition, as an example, the nuclear spin isotope(s) can include noble gas isotopes. The cell system 102 also includes a magnetic field generator 110 that is configured to generate a magnetic field $B_E$. As an example, the magnetic field generator 110 can be configured as a magnetic solenoid that substantially surrounds the sensor cell 106 to generate the magnetic field $B_E$ as a substantially uniform magnetic field. In response to the magnetic field $B_E$, the particles of the alkali metal 108 and the nuclear spin isotopes can precess relative to an axis of the sensor cell 106.

The cell system 102 also includes a pump laser 112. The pump laser 112 can be configured to generate an optical pump beam $O_{PMP\_S}$ having a linear polarization (e.g., the "s" polarization). The optical pump beam $O_{PMP\_S}$ is directed through a beamsplitter 114 and a quarter-wave plate 116. The quarter-wave plate 116 is configured to change the linear polarization of the optical pump beam $O_{PMP\_S}$ to a circular polarization, demonstrated as the optical pump beam $O_{PMP\_C}$. The optical pump beam $O_{PMP\_C}$ is directed through the sensor cell 106 to stimulate (i.e., excite) the particles of the alkali metal 108 to a polarized state. In the example of FIG. 3, the optical pump beam $O_{PMP\_C}$ is directed through the sensor cell 106 twice based on reflection of the optical pump beam $O_{PMP\_C}$ from a mirror 118 at a distal side of the sensor cell 106, with the reflected optical pump beam being demonstrated as $O_{PMP\_C}'$. Thus, optical pumping of the particles of the alkali metal 108 can be substantially increased.

The reflected optical pump beam $O_{PMP\_C}'$ exiting the sensor cell 106 is directed through the quarter-wave plate 116, thus transforming the circular polarization to a linear polarization. However, the linear polarization of the optical pump beam is oriented orthogonally with respect to the optical pump beam $O_{PMP\_S}$ provided by the pump laser 112, and is thus demonstrated as optical pump beam $O_{PMP\_P}$ to denote the "p" polarization. Therefore, upon being provided to the beamsplitter 114, the optical pump beam $O_{PMP\_P}$ is reflected and directed to the pump beam control system 104. Accordingly, the pump beam control system 104 can monitor optical absorption of the optical pump beam $O_{PMP\_C}$ based on the intensity of the optical pump beam $O_{PMP\_P}$. As described herein, optical absorption of the optical pump beam $O_{PMP\_C}$ denotes a collective optical absorption of the optical pump beams $O_{PMP\_C}$ and $O_{PMP\_C}'$.

As described herein, the particles of the alkali metal 108 can be subject to AC Stark shift, in which the optical pumping of the particles of the alkali metal 108 via the pump laser 112 is off-resonance with respect to one or both atomic transition wavelengths corresponding to two independent ground states of the alkali metal 108. To ensure that the AC Stark shift is measurable, the pump laser 112 can be oriented to generate the optical pump beam $O_{PMP\_C}$ at an offset angle θ with respect to the applied magnetic field $B_E$. For example, the pump laser 112 can be physically oriented at the offset angle θ, such that the optical pump beam $O_{PMP\_C}$ is provided through the sensor cell 106 at the offset angle θ, or the cell system 102 can include additional optics to provide the optical pump beam $O_{PMP\_C}$ through the sensor cell 106 at the offset angle θ.

The pump beam control system 104 includes a stabilization system 120 and a photodetector 122. The stabilization system 120 includes a PWM controller 124. The stabilization system 120 is configured to generate a modulation current $I_{MOD}$ that is provided to the pump laser 112. Therefore, the amplitude and frequency of the pump laser 112 can be set based on a magnitude of the modulation current $I_{MOD}$. The stabilization system 120 can thus pulse-width modulate the magnitude of the modulation current $I_{MOD}$ based on the PWM controller 124. As a result, the frequency of the optical pump beam $O_{PMP\_S}$ provided by the pump laser 112 is pulse-width modulated to have a duty-cycle, as provided by the PWM controller 124, such that the absorption of the optical pump beam $O_{PMP\_C}$ varies inter alia as a function of the amplitudes of the respective portions of the duty-cycle, similar to as demonstrated in the example of FIG. 2. Thus, the optical pump beam $O_{PMP\_C}$ is pulse-width modulated.

The optical pump beam $O_{PMP\_P}$ is provided from the beamsplitter 114 to the photodetector 122, such that the photodetector 122 is configured to generate an absorption voltage $V_{DET}$ that corresponds to the intensity of the optical pump beam $O_{PMP\_P}$, which thus corresponds to the absorption of the optical pump beam $O_{PMP\_C}$ in the sensor cell 106. The absorption voltage $V_{DET}$ is provided to the stabilization system 120, such that the stabilization system 120 can monitor the absorption of the optical pump beam $O_{PMP\_C}$ based on the absorption voltage $V_{DET}$. Because the frequency of the optical pump beam $O_{PMP\_C}$ varies based on the duty-cycle, the absorption voltage $V_{DET}$ likewise varies at approximately the duty-cycle. Therefore, the stabilization system 120 can be configured to determine the absorption spectrum of the optical pump beam $O_{PMP\_P}$ as a time-average through the pulse-width modulation period. As a result, the stabilization system 120 can determine a frequency of the optical pump beam $O_{PMP\_S}$ generated by the pump laser 112 that corresponds to substantial maximum absorption of the optical pump beam $O_{PMP\_C}$ through the sensor cell 106 (e.g., the center of the frequency band between the transition frequencies).

In the example of FIG. 3, the sensor system 100 also includes a detection system 126 that is configured to calculate at least one measurable parameter. For example, the measurable parameter can include rotation about a sensitive axis in the example of the sensor system 100 being configured as an NMR gyroscope, or can include a vector magnitude of an external magnetic field in the example of the sensor system 100 being configured as an NMR/EPR magnetometer. In the example of FIG. 3, the detection system 126 includes a probe laser 128, a rotation detector 130, and a measurement controller 132. The probe laser 128 can be configured to generate a probe beam $O_{PRB}$ that passes through the sensor cell 106. The precession of the particles of the alkali metal 108 and the associated nuclear spin isotopes can result in phase changes associated with a detection beam $O_{DET}$ corresponding to the probe beam exiting the sensor cell 106. The detection beam $O_{DET}$ is provided to the rotation detector 130, which is configured to generate a signal FAR that is indicative of the Faraday rotation of the detection beam $O_{DET}$. Therefore, the measurement controller 132 can calculate the measurable parameter based on changes in the precession of the particles of the alkali metal 108, such as resulting from rotation of the sensor cell 106 or an external magnetic field, which is indicated by the Faraday rotation of the detection beam $O_{DET}$ as provided by the signal FAR.

In addition, as described previously, the optical pump beam $O_{PMP\_C}$ can be oriented at an offset angle θ with respect to the applied magnetic field $B_E$. As a result, the AC Stark shift induces an AC virtual magnetic field $B_L$ in a vector direction that is orthogonal to the applied magnetic field $B_E$ based on vector components of the optical pump beam $O_{PMP\_C}$ in the plane orthogonal to the applied magnetic field $B_E$. The induced AC magnetic field $B_L$ can thus likewise vary based on the duty-cycle of the optical pump beam $O_{PMP\_S}$. Therefore, the AC magnetic field $B_L$ can affect the precession of the alkali metal 108 at the duty-cycle. As a result, in addition to the Faraday rotation of the detection beam $O_{DET}$ resulting from the rotation of the sensor cell 106 or an external magnetic field, the detection beam $O_{DET}$ can have a Faraday rotation that varies at the duty-cycle resulting from the induced magnetic field $B_L$.

The rotation detector 130 can thus also provide the signal FAR to the stabilization system 120. Thus, the stabilization system 120 can be configured to demodulate the signal FAR based on the duty-cycle, such that the stabilization system 120 can determine an effect of the AC Stark shift on the detection beam $O_{DET}$. The stabilization system 120 can thus obtain a DC error signal having a magnitude and a sign that corresponds to the effects of the AC Stark shift, and thus a deviation from a duty-cycle of the optical pump beam $O_{PMP\_S}$ at which the effects of the AC Stark shift are equal and opposite. As a result, the stabilization system 120 can adjust the duty-cycle of the pump beam $O_{PMP\_S}$ based on the DC error signal to substantially minimize the DC error signal (e.g., set to a zero value) in a feedback manner. Thus, upon the DC error signal being approximately equal to zero, the time-averaged frequency of the optical pump beam $O_{PMP\_S}$ over the pulse-width modulation period is approximately equal to the frequency value at which the effects of the AC Stark shift are approximately equal and opposite with respect to excitation of the particles of the alkali metal 108 out of the two independent ground states.

Therefore, the stabilization system 120 can continuously demodulate the signal FAR at the duty-cycle to monitor the Faraday rotation of the detection beam $O_{DET}$ and can adjust the duty-cycle of the optical pump beam $O_{PMP\_S}$ based on the modulation current $I_{MOD}$ in a feedback manner. As a result, the time-averaged frequency of the PWM pump beam $O_{PMP\_S}$, and thus the optical pump beam $O_{PMP\_C}$, is maintained at a frequency at which the effects of the AC Stark shift are equal and opposite with respect to the two independent ground states of the alkali metal 108. Accordingly, based on the feedback pulse-width modulation of the optical pump beam $O_{PMP\_S}$ by the stabilization system 120, the stabilization system 120 stabilizes the AC Stark shift while maintaining off-resonance pumping of the alkali metal vapor 108 to substantially maximize polarization uniformity of the alkali metal vapor 108 to improve performance of the sensor system 100 in measuring the measurable parameter. Furthermore, because the time-averaged AC Stark shift effects are substantially equal and opposite based on the PWM duty-cycle, the AC Stark shift effects are substantially mitigated. Accordingly, scale factor and bias errors associated with the measurable parameter(s) of the sensor system 100 is likewise substantially mitigated.

In addition, as described previously, absorption of the optical pump beam $O_{PMP\_C}$ is based in part on temperature of the sensor cell 106. In the example of FIG. 3, the cell system 102 also includes a cell temperature controller 134 that is configured to set the temperature of the sensor cell 106. The stabilization system 120 can be configured to stabilize the temperature of the sensor cell 106 via the cell temperature controller 134 based on the monitored absorption of the optical pump beam $O_{PMP\_C}$ via the absorption voltage $V_{DET}$. As an example, the stabilization system 120 can determine changes in the absorption of the optical pump beam $O_{PMP\_C}$ based on the demodulated absorption voltage $V_{DET}$ and can provide a temperature control signal TEMP_CTRL to the cell temperature controller 134 to modify the temperature of the sensor cell 106 to substantially compensate for the changes in absorption of the optical pump beam $O_{PMP\_C}$. Therefore, the stabilization system 120 can likewise stabilize the temperature of the sensor cell 106 based on the absorption voltage $V_{DET}$ in a feedback manner to provide for substantially optimal absorption of the optical pump beam $O_{PMP\_C}$.

Figure 4:
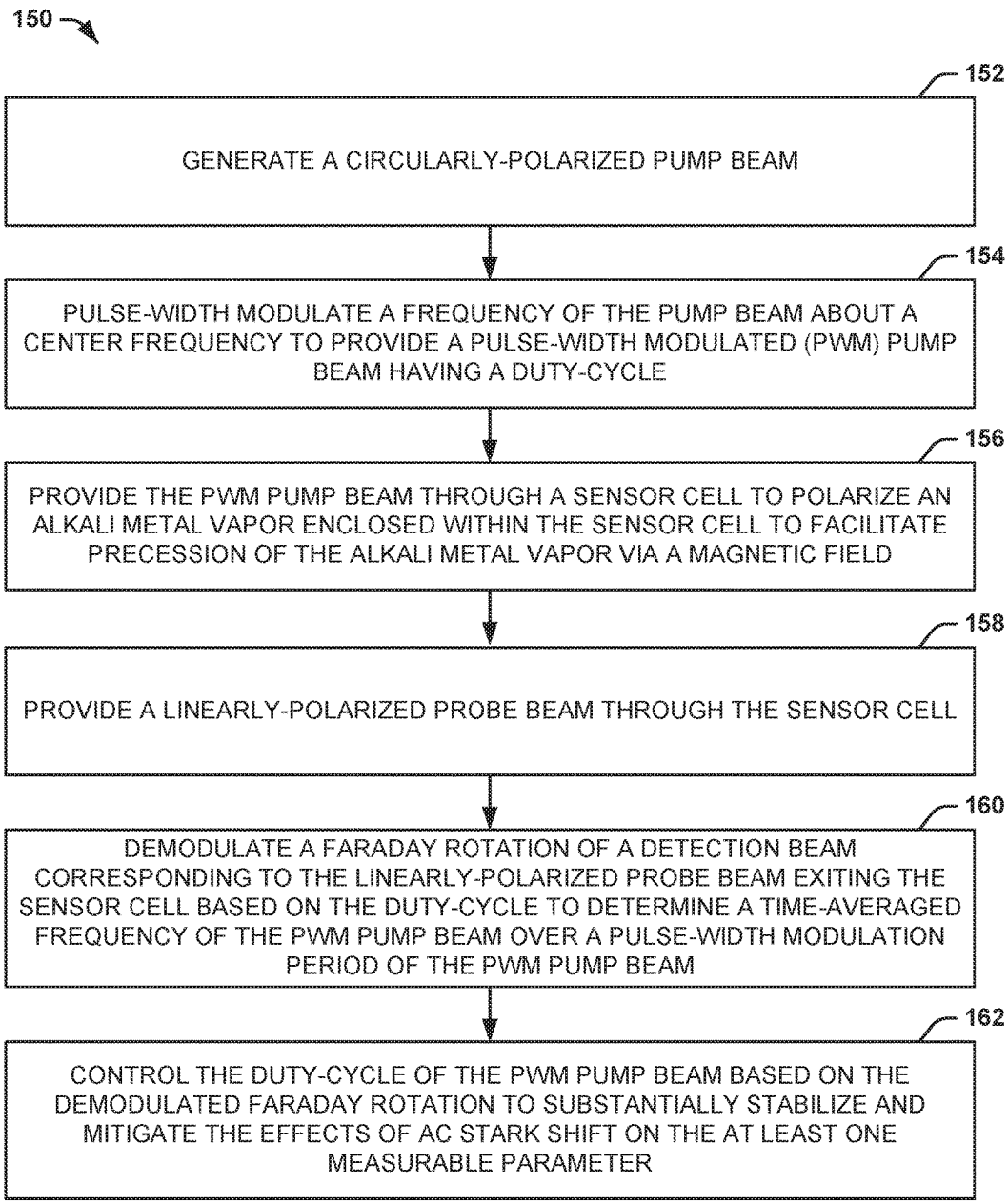
FIG. 4 illustrates an example of a method for controlling an optical pump beam in a sensor system.

In view of the foregoing structural and functional features described above, a methodology in accordance with various aspects of the present invention will be better appreciated with reference to FIG. 4. While, for purposes of simplicity of explanation, the methodology of FIG. 4 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 4 illustrates an example of a method 150 for substantially mitigating AC Stark shift effects in a sensor system (e.g., the sensor system 10). At 152, a circularly-polarized pump beam (e.g., the optical pump beam $O_{PMP\_S}$) is generated. At 154, a frequency of the pump beam is pulse-width modulated about a center frequency (e.g., the wavelength $\lambda_C$) to provide a PWM pump beam having a duty-cycle (e.g., the "ON" time 58 and the "OFF" time 60). At 156, the PWM pump beam is provided through a sensor cell (e.g., the sensor cell 14) to polarize an alkali metal vapor (e.g., the alkali metal vapor 18) enclosed within the sensor cell to facilitate precession of the alkali metal vapor via a magnetic field (e.g., the magnetic field $B_E$). At 158, a linearly-polarized probe beam (e.g., the probe beam $O_{PRB}$) is provided through the sensor cell. At 160, a Faraday rotation of a detection beam (e.g., the detection beam $O_{DET}$) corresponding to the linearly-polarized probe beam exiting the sensor cell is demodulated based on the duty-cycle to determine a time-averaged frequency of the PWM pump beam over a pulse-width modulation period of the PWM pump beam. At 162, the duty-cycle of the PWM pump beam is controlled based on the demodulated Faraday rotation to adjust the time-averaged frequency to substantially stabilize and mitigate the effects of AC Stark shift on the at least one measurable parameter.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A sensor system comprising:
   a cell system comprising a pump laser configured to generate a pump beam to polarize alkali metal vapor enclosed within a sensor cell;
   a detection system comprising a probe laser configured to generate a probe beam, the detection system being configured to calculate at least one measurable parameter based on characteristics of the probe beam passing through the sensor cell resulting from precession of the polarized alkali metal vapor in response to an applied magnetic field; and
   a pump beam control system configured to pulse-width modulate a frequency of the pump beam to provide a pulse-width modulated (PWM) pump beam, and to control a duty-cycle of the PWM pump beam based on the characteristics of the probe beam passing through the sensor cell in a feedback manner to control polarization uniformity of the alkali metal vapor and to mitigate the effects of AC Stark shift on the at least one measurable parameter.

2. The system of claim 1, wherein the pump beam control system is configured to control the duty-cycle in the feedback manner to maintain the duty-cycle at which the effects of the AC Stark shift are substantially equal and opposite with respect to a pulse-width modulation period of the PWM pump beam based on the characteristics of the probe beam passing through the sensor cell.

3. The system of claim 1, wherein the sensor system is configured as at least one of a nuclear magnetic resonance (NMR) gyroscope, an NMR magnetometer, and an electron paramagnetic resonance (EPR) magnetometer.

4. The system of claim 1, wherein the pump beam control system comprises a stabilization system configured to generate a current that is provided to the pump laser to set the frequency of the pump beam to each of a first frequency and a second frequency corresponding to the duty-cycle of the PWM pump beam, the stabilization controller comprising a PWM controller configured to control an amplitude of the current to set the duty-cycle of the PWM pump beam based on a Faraday rotation of the probe beam.

5. The system of claim 4, wherein the pump laser is oriented to provide the PWM pump beam at an offset angle with respect to the applied magnetic field to generate an induced virtual magnetic field internal to the sensor cell that is substantially coplanar with the probe beam corresponding to the effects of the AC Stark shift, the induced virtual magnetic field providing the Faraday rotation of the probe beam to be approximately equal to the duty-cycle of the PWM pump beam.

6. The system of claim 4, wherein the stabilization system is configured to control the duty-cycle of the PWM pump beam based on demodulating the Faraday rotation of the probe beam by the duty-cycle to substantially maintain the duty-cycle of the PWM pump beam at a duty-cycle at which the effects of the AC Stark shift are substantially at a time-averaged zero magnitude.

7. The system of claim 1, wherein the pump beam control system is configured to monitor an optical absorption of the PWM pump beam and to pulse-width modulate the frequency of the pump beam about a center frequency corresponding to an approximate maximum absorption of the PWM pump beam via the alkali metal vapor.

8. The system of claim 7, wherein the cell system further comprises a cell temperature controller configured to set a temperature of the sensor cell via a feedback temperature control signal to substantially stabilize a time-averaged optical absorption of the PWM pump beam passing through the sensor cell based on the monitored optical absorption of the PWM pump beam.

9. The system of claim 7, wherein the pump beam control system comprises a stabilization system configured to digitally adjust the duty-cycle of the PWM pump beam based on setting a number of clock pulses of the PWM pump beam in a first frequency and a number of clock pulses of the PWM pump beam in a second frequency relative to a fixed number of clock pulses of a pulse-width modulation period, wherein the first and second frequencies are substantially equal and opposite with respect to the center frequency.

10. A sensor system comprising:
    a cell system comprising a pump laser configured to generate a pump beam to polarize alkali metal vapor enclosed within a sensor cell and to facilitate precession of the alkali metal vapor in response to an applied magnetic field, the pump beam being provided through the sensor cell at an offset angle relative to the applied magnetic field;
    a detection system comprising a probe laser configured to generate a probe beam, the detection system being configured to calculate at least one measurable parameter based on characteristics of the probe beam passing through the sensor cell resulting from precession of the polarized alkali metal vapor in response to the applied magnetic field; and a pump beam control system configured to pulse-width modulate a frequency of the pump beam about a center frequency corresponding to an approximate maximum absorption of the pump beam via the alkali metal vapor to provide a pulse-width modulated (PWM) pump beam having a duty-cycle, to demodulate a detection beam corresponding to the probe beam exiting the sensor cell based on the duty-cycle, and to control the duty-cycle of the PWM pump beam based on the demodulated detection beam in a feedback manner to control polarization uniformity of the alkali metal vapor and to mitigate the effects of AC Stark shift on the at least one measurable parameter.

11. The system of claim 10, wherein the pump beam control system is configured to control the duty-cycle in the feedback manner to maintain the duty-cycle at which the effects of the AC Stark shift are substantially equal and opposite with respect to a pulse-width modulation period of the PWM pump beam based on the characteristics of the probe beam passing through the sensor cell.

12. The system of claim 10, wherein the pump beam control system comprises a stabilization system configured to generate a current that is provided to the pump laser to set the frequency of the pump beam between a first frequency and a second frequency corresponding to the duty-cycle of the PWM pump beam, the stabilization controller comprising a PWM controller configured to control an amplitude of the current to set the duty-cycle of the PWM pump beam based on a Faraday rotation of the probe beam, the first and second frequencies being approximately equal and opposite with respect to the center frequency.

13. The system of claim 10, wherein the cell system further comprises a cell temperature controller configured to set a temperature of the sensor cell via a feedback temperature control signal to substantially stabilize a time-averaged optical absorption of the PWM pump beam passing through the sensor cell based on the monitored optical absorption of the PWM pump beam.

14. The system of claim 10, wherein the pump beam control system comprises a stabilization system configured to digitally adjust the duty-cycle of the PWM pump beam based on setting a number of clock pulses of the PWM pump beam in a first frequency and a number of clock pulses of the PWM pump beam in a second frequency relative to a fixed number of clock pulses of a pulse-width modulation period, wherein the first and second frequencies are substantially equal and opposite with respect to the center frequency.

* * * * *